United States Patent [19]

Sharp et al.

[11] 3,958,557

[45] May 25, 1976

[54] CORONARY ARTERY BYPASS GRAFT TESTING DEVICE AND METHOD

[75] Inventors: Russell G. Sharp, Sugar Land; Denton A. Cooley; Charles C. Reed, both of Houston, all of Tex.

[73] Assignee: Texas Medical Products, Inc., Houston, Tex.

[22] Filed: Mar. 10, 1975

[21] Appl. No.: 556,613

[52] U.S. Cl. .............................. 128/1 R; 128/348; 128/303 R; 3/1.4; 73/49.1; 138/90
[51] Int. Cl.² ...................... A61B 19/00; A61F 1/24
[58] Field of Search ............. 128/1 R, 214 R, 214.4, 128/221, 348, 303 R; 3/1, 1.4; 73/40.5 R, 49.1, 49.5; 138/90

[56] References Cited
UNITED STATES PATENTS

| | | | |
|---|---|---|---|
| 3,094,124 | 6/1963 | Birtwell | 128/348 |
| 3,490,438 | 1/1970 | Lavender et al. | 128/214 R X |
| 3,916,874 | 11/1975 | Perrin | 128/1 R |

FOREIGN PATENTS OR APPLICATIONS

| | | | |
|---|---|---|---|
| 1,520,783 | 3/1968 | France | 128/221 |
| 291,315 | 5/1928 | United Kingdom | 128/221 |

OTHER PUBLICATIONS

"New Teflon Intravascular Catheter", by R. A. Gaertner, *Surgery, Gynecology & Obstetrics,* Vol. 119, No. 3, Sept. 1964, pp. 599–600.

*Primary Examiner*—Ronald L. Frinks
*Attorney, Agent, or Firm*—H. Ross Workman; J. Winslow Young

[57] ABSTRACT

A device and method for preparation and testing of a blood vessel such as the saphenous vein for use as a coronary bypass graft. The device includes a hollow body portion and a hollow stylet projecting therefrom. The stylet presents a peripheral flange facilitating temporary ligation of the vein upon the catheter. The body has a Luer fitting to accommodate coupling with a conventional syringe.

6 Claims, 2 Drawing Figures

CORONARY ARTERY BYPASS GRAFT TESTING DEVICE AND METHOD

BACKGROUND

1. Field of the Invention

The invention relates to a surgical testing device and method and more particularly to novel structure and method for preparing and testing veins for coronary bypass grafts.

2. The Prior Art

Myocardial ischemia is a deficiency of blood in the heart due to a functional constriction or actual obstruction of coronary arteries. Presently, this cardiac disease is the most common affecting mankind in modern society. Only recently has direct arterial surgery been utilized effectively to control the symptoms and prolong useful life in patients afflicted by coronary disease of this type.

One of the most successful and well accepted techniques for surgically relieving myocardial ischemia is the saphenous vein autograft. In a preferred embodiment of this technique, direct immediate revascularization is accomplished by proximal anastomosis in the ascending aorta and distal end-to-side anastomosis to the coronary artery below the obstruction. Care is taken to reverse the saphenous vein so that the valves in the vein will not interfere with blood flow through by bypass. Anastomosis is defined herein as the surgical formation of a passage between two normally distinct blood vessels.

The foregoing technique has been found to be highly successful with properly tested and treated saphenous vein grafts. The great saphenous vein is the longest vein in the body extending from the dorsum of the foot to just below the inguinal ligament where it opens into the femoral vein. The saphenous vein is normally obtained from the groin through the same incision required to expose the femoral artery for cannulation involved in connecting the patient to the heart-lung machine in the course of this surgery. The incision may be extended to approximately the beginning of the upper part of the thigh in order to obtain an adequate length of the saphenous vein.

Historically, the selection of the particular segment of saphenous vein has proved critically important and has posed serious difficulty. For example, after the tributaries of the selected portion of saphenous vein have been tied off and severed, it must be ascertained that the selected saphenous vein segment is free of occlusions and clots. Further, any leaks in the segment at the sites of the severed tributaries must be detected and the distensibility index determined. Finally, the vein must be pre-sized to insure that the vein segment will carry an adequate supply of blood and at the same time facilitate anastomosis.

Determination of the foregoing parameters can be accomplished in part by subjecting the vein segment to fluid irrigation and hydrostatic pressure administered to the interior of the saphenous vein through a syringe. Conventional cannulas, however, have proved cumbersome and difficult to use both because of their length and external configuration in preparing and testing the saphenous vein segment. Until this present invention, no prior art device has been provided which would adequately accommodate the preparation and testing required by this highly sophisticated surgical technique.

BRIEF SUMMARY AND OBJECTS OF THE INVENTION

The present invention is a proving device and method to prove and test blood vessels such as the saphenous vein for use as a coronary bypass graft. The device, in the general form of a cannula has a stylet sized to correspond generally with the undistended internal diameter of an appropriate vein segment and presents a peripheral flange accommodating temporary pressure-tight ligation of the vein and cannula. The cannula also presents structure accommodating irrigation and pressure testing of the vein through the cannula.

It is, therefore, a primary object of the present invention to provide a novel proving device construction.

It is another primary object of the present invention to provide improved method for proving and testing a blood vessel segment for use as a coronary bypass graft.

It is another desirable object of the present invention to provide an improved device and method for pre-sizing a vein to be used in aorta-coronary bypass graft surgery.

These and other objects and features of the present invention will become more fully apparent from the following description and appended claims taken in conjunction with the accompanying drawing.

DETAILED DESCRIPTION OF THE PREFERRED EMBODIMENT

Figure 1:
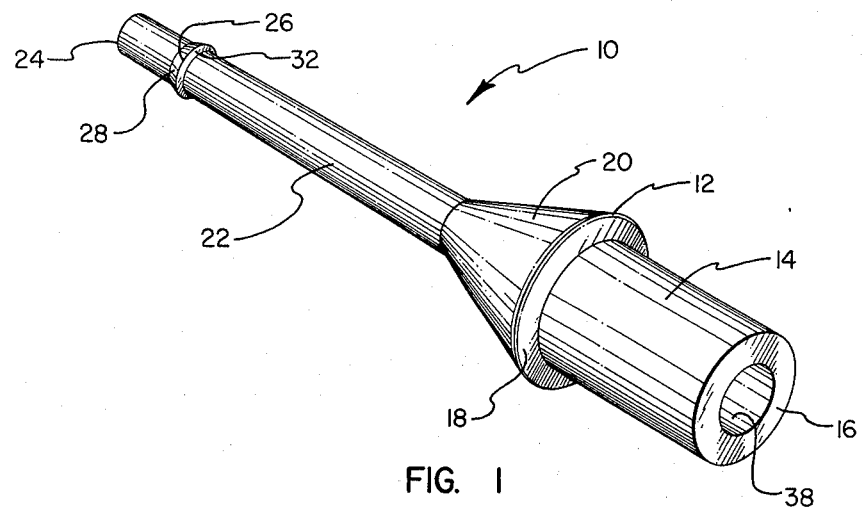
FIG. 1 is a perspective view of one presently preferred embodiment of the invention.

Reference is now made to FIG. 1 which illustrates a cannula generally designated 10. The cannula is preferably molded as a one-piece unit of medical grade polyethylene having suitable flexibility and softness required to prevent trauma to the intima of the vein in which it is used. The cannula 10 has a hub 14 at the proximal end thereof which is essentially cylindrical in configuration and terminates in a flat essentially planar surface 16. The hub 14 is connected to a body 12 which is diametrally enlarged to form a shoulder 18 in a plane parallel to the surface 16. The hub 14 is sized to accommodate coupling with conventional surgical tubing (not shown) which may be press-fit upon the hub and abut shoulder 18. The body 12 is frustoconical in configuration the forwardly tapering ramp surface 20 merging with the stylet 22 which forms the distal end of the cannula 10.

The stylet 22 has a very gradual taper from the body 12 to the distal end 24. The external dimension of the stylet 22 is selected to be essentially the normal internal diameter of a suitable vein segment for use in coronary bypass. Thus, the cannula stylet 22 serves as a guide to the selection of an appropriate sized vein segment.

Importantly, the stylet 22 presents a peripheral flange 26 spaced slightly behind the distal end 24. The peripheral flange 26 is integral with the stylet 22 and has a forwardly tapering ramp surface 28 which facilitates insertion of the stylet 22 into a suitable vein segment 30 (see FIG. 2). The flange 26 terminates in a shoulder 32 which permits pressure-tight ligation as will be hereinafter more fully described.

Figure 2:
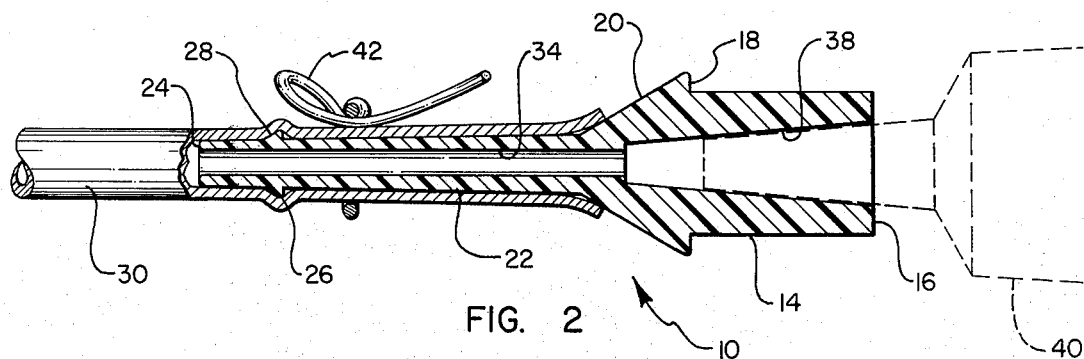
FIG. 2 is a longitudinal cross section of the embodiment of FIG. 1, the catheter of FIG. 1 being illustrated in the environment of pressure testing, a portion of the environment being illustrated in broken lines.

The interior of the cannula 10 is hollow as best shown in FIG. 2. More specifically, the stylet 22 has an annular bore 34 which opens at the distal end 24 and is also in open communication with hollow 38 in the hub 14. The hollow 38 is coaxial with the bore 34 and is provided with a Luer taper so as to form a female coupling. Thus, the cannula 10 may be press-coupled to a suitable irrigation instrument such as a syringe 40.

The method of the invention will be described in connection with the saphenous vein although presumably other blood vessels could conceivably be used for arterial bypass purposes. The saphenous vein is exposed, for example, in the groin area. The particular segment of the vein selected for the graft may be determined by its size, measured in part by the surgeon's visual comparison of the vein with the stylet 22 of the cannula 10. The vein tributaries along the length of the selected vein segment are severed from the vein segment after ligature. The selected portion of the vein is then severed and the stylet 22 inserted within the lumen of the resected vein 30 until the vein is pressed tightly upon the ramp surface 20. Tactile evaluation of resistance to the insertion of the stylet 22 within the lumen of the vein also serves as a measure of appropriate vein size to the skilled surgeon. Thereafter, temporary ligation is effected by tying suture 42 tightly around the vein in the vicinity of the flange 26. Ligation will have the effect of creating a fluid seal between the vein segment 30 and the cannula 10.

Thereafter, a syringe 40 or the like may be used for irrigating purposes to determine whether occlusions or clots remain in the vein segment and, if so, to accommodate flushing of the vein. Further, a distant portion of the vein segment can be clamped or otherwise occluded and hydrostatic pressure communicated to the vein through the cannula 10 with the syringe 40. The hydrostatic pressure can be used to detect leaks in the vein segment 30 particularly at the severed tributary sites. The hydrostatic pressure also serves to determine the distensibility index of the vein. If the vein distends too easily under pressure, it is not suitable for coronary artery bypass. It is significant that the vein segment 30 will not be forced off the stylet 22 because of the flange 26 which will not pass through the temporary ligation at 42. After the vein has been proven, the appropriate segment may be used for the coronary artery bypass.

The invention may be embodied in other specific forms without departing from its spirit or essential characteristics. The described embodiment is to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A coronary artery bypass graft proving device comprising:

an elongated hollow stylet fabricated from a material having suitable flexibility and softness to prevent trauma to the intima of a vein, the stylet having a blunt end and being adapted to be telescopically inserted within a portion of the vein;

an annular raised flange situated intermediate the insertable length of the stylet, the flange having a rearwardly tapering ramp surface to facilitate insertion of the stylet and flange into a vein segment, the flange terminating in a flange shoulder thereby serving to engage the interior of the vein to facilitate fluid-tight ligation of the vein on the stylet;

a frustoconical body forming a ramp against which the end of the vein is pressed, the ramp being integral with and tapering away from the stylet, the ramp extending outwardly to a diametrally enlarged body shoulder, the body terminating in a diametrally reduced, cylindrical coupling member, the body shoulder forming an abutment surface for tubing placed on the coupling member; and a female Luer fitting interior of the body.

2. A coronary artery bypass graft proving device as defined in claim 1 wherein the hollow stylet is dimensionally sized with a gradual taper to correspond to the necessary internal diameter of a coronary artery bypass graft thereby serving as a guide to the necessary graft vein size.

3. A method of proving a graft segment for use in coronary artery bypass the steps of:

obtaining a cannula having a stylet presenting an annular flange and generally corresponding in external diameter with the internal diameter of the required graft segment;

inserting the cannula into an exposed portion of a saphenous vein;

forming a temporary ligature over the cannulated portion of the vein above the annular flange so that the flange will be urged against the ligature without expulsion of the cannula when hydrostatic pressure builds in the vein;

occluding a distant portion of the vein and attaching a fluid delivery system to the cannula; and exerting fluid pressure upon the lumen of the cannulated vein by forcing the fluid through the cannula.

4. A method of proving a graft segment for use in coronary artery bypass as defined in claim 3 wherein said inserting step comprises tactilely evaluating the diameter of the vein by sensing the resistance of the vein to penetration by the catheter.

5. A method or proving a graft segment for use in coronary artery bypass as defined in claim 3 further comprising irrigating the resected vein through the cannula.

6. A method of proving a graft segment for use in coronary artery bypass as defined in claim 3 further comprising removing the temporary ligature and thereafter removing the cannula from the vein prior to anastomosis with the coronary artery.

* * * * *